(12) United States Patent
Streicher et al.

(10) Patent No.: US 6,409,969 B1
(45) Date of Patent: Jun. 25, 2002

(54) SYSTEM AND METHOD FOR CONTROLLING A SELF-HEATED GAS SENSOR BASED ON SENSOR IMPEDANCE

(75) Inventors: Steven R. Streicher, Cincinnati, OH (US); James A. Freeman, Antioch, IL (US); John E. Taylor, Columbus, IN (US)

(73) Assignee: Cummins, Inc., Columbus, IN (US)

( * ) Notice: Subject to any disclaimer, the term of this patent is extended or adjusted under 35 U.S.C. 154(b) by 0 days.

(21) Appl. No.: 09/323,199

(22) Filed: Jun. 1, 1999

(51) Int. Cl.$^7$ .............................................. G01N 31/12
(52) U.S. Cl. ............................ 422/94; 422/98; 422/83
(58) Field of Search ............................ 422/94, 51, 90; 73/25.01; 60/274; 324/706; 219/497

(56) References Cited

U.S. PATENT DOCUMENTS

| | | | |
|---|---|---|---|
| 4,504,732 A | * 3/1985 | Bube et al. ................. 219/497 |
| 4,958,611 A | 9/1990 | Uchinami et al. |
| 4,993,392 A | 2/1991 | Tanaka et al. |
| 5,036,470 A | 7/1991 | Suzuki et al. |
| 5,067,465 A | 11/1991 | Yamasaki et al. |
| 5,090,387 A | 2/1992 | Mayer et al. |
| 5,111,792 A | 5/1992 | Nagai et al. |
| 5,148,795 A | 9/1992 | Nagai et al. |
| 5,172,678 A | 12/1992 | Suzuki |
| 5,225,786 A | * 7/1993 | Vaughn et al. ............... 324/706 |
| 5,245,979 A | 9/1993 | Pursifull et al. |
| 5,291,673 A | * 3/1994 | Hamburg et al. .............. 60/274 |
| 5,482,678 A | * 1/1996 | Sittler .......................... 422/90 |
| 5,485,382 A | 1/1996 | Seki et al. |
| 5,505,183 A | 4/1996 | Sinha et al. |
| 5,522,250 A | * 6/1996 | Gee et al. ..................... 73/1 G |
| 5,588,417 A | 12/1996 | Kotwicki et al. |
| 5,596,975 A | 1/1997 | Thomas et al. |
| 5,605,040 A | 2/1997 | Cullen et al. |
| 5,671,721 A | 9/1997 | Aoki |
| 5,708,585 A | 1/1998 | Kushion |
| 5,804,703 A | * 9/1998 | Wind et al. ................. 73/25.01 |
| 5,958,340 A | * 9/1999 | Meyer et al. .................. 422/90 |
| 6,071,476 A | * 6/2000 | Young et al. .................. 422/51 |
| 6,126,902 A | * 10/2000 | Kunimoto et al. ............. 422/94 |
| 6,173,602 B1 | * 1/2001 | Moseley et al. ........... 73/31.06 |

* cited by examiner

Primary Examiner—Jill Warden
Assistant Examiner—Brian Sines
(74) Attorney, Agent, or Firm—Barnes & Thornburg

(57) ABSTRACT

The present invention contemplates a system and method for controlling or adjusting the accuracy of an exhaust gas sensor utilizing the impedance of the sensing element. In one embodiment, a periodic AC signal is superimposed over low frequency or DC output signal produced by the gas sensor. The AC current flowing through the gas sensor is a function of the actual impedance of the sensor, which is in turn a function of the temperature of the sensor. Thus, the invention further contemplates an impedance sensor circuit connected to an output of the gas sensor. The output of the impedance sensor circuit is a peak voltage that is indicative of the AC voltage drop across the sensor, and ultimately the impedance of the sensing element. This peak voltage is utilized to control the operation of the heating element in a closed loop control system in which the thermal output of the heating element is continuously varied as a function of the magnitude signal to accurately maintain a consistent temperature for the exhaust gas sensor. In a specific embodiment of the invention, the impedance sensor circuitry includes a bandpass filter centered around the frequency of the superimposed AC signal to eliminate spurious noise. The output from the bandpass filter is provided to a half-wave rectifier, the output of which is the peak voltage signal indicative of the sensor impedance.

25 Claims, 2 Drawing Sheets

SYSTEM AND METHOD FOR CONTROLLING A SELF-HEATED GAS SENSOR BASED ON SENSOR IMPEDANCE

BACKGROUND OF THE INVENTION

The present invention relates to a system and method for controlling the performance of an exhaust gas sensor. More specifically, the invention pertains to controlling a self-heated sensor based upon the impedance of the sensor.

State and national regulations for vehicle emissions have required engine manufactures to maintain tight control over engine performance. As a result, most modern internal combustion engines utilize an electronic control module (ECM) that receives data from various sensors throughout the engine. The ECM then generates signals controlling various components of the engine.

In order to maintain optimum engine performance while reducing noxious emissions, it is highly desirable to control the air/fuel mixture provided to the engine within stoichiometric ratios. In certain applications, it is desirable to maintain the air/fuel mixture at a specific lean-burn ratio. In most electronically controlled engines, this ratio is determined in relation to the detected intake air quantity, detected engine speed and a base fuel amount, as well as data from the engine sensors. In more sophisticated engine control systems, a corrected fuel amount is generated based upon the gas content of the engine exhaust.

More specifically, the gas content of the engine exhaust provides a measure for engine combustion performance, which in turn is a function of the air/fuel mixture being provided to the engine. For example, if the air/fuel mixture is rich, the engine exhaust will include a lower than normal concentration of oxygen ($O_2$). On the other hand, if the air/fuel ratio is too lean, $NO_x$ emissions in the engine exhaust increase.

In order to accurately regulate the air/fuel mixture to acceptable proportions (e.g., stoichiometric or lean-burn), most engines include an exhaust gas sensor disposed within the engine exhaust conduit. Most typically, the sensor is an oxygen sensor that generates an output signal in relation to the concentration of oxygen ($O_2$) passing through the sensor.

One problem encountered by a typical exhaust gas oxygen sensor is that the output of the sensor is temperature dependent. For most internal combustion engines, the exhaust temperature can vary significantly, which can lead to detrimental perturbations in the sensor output that may not be indicative of changes in $O_2$ concentration. The effect of temperature variations can be more significant in lean-burn applications.

In order to address this problem, most exhaust gas sensors are self-heated, meaning that a heating element is disposed immediately adjacent the sensor to elevate its temperature. When the sensor is calibrated at the elevated temperature, the normal temperature variations of the exhaust gas flow have a much less significant impact on the accuracy of the sensor output. For instance, exhaust gas temperatures will typically range from ambient to about 400° C. In many known exhaust gas oxygen sensors, the heating element heats the sensing element to 800–900° C.

Even with this improvement, the accuracy of the output of most known exhaust oxygen sensors is less than optimum. There remains a need in the industry for an exhaust gas sensor that can maintain accurate gas level readings in spite of variations in the engine exhaust temperature.

SUMMARY OF THE INVENTION

In order to address this need, the present invention contemplates a system and method for controlling or adjusting the accuracy of an exhaust gas sensor utilizing the impedance of the sensor. In one embodiment, a periodic AC signal is superimposed on the low frequency or DC voltage signal output of the gas sensor. The AC current flowing through the gas sensor is a function of the actual impedance of the sensor, which is in turn a function of the temperature of the sensor. Thus, the invention further contemplates an impedance sensor circuit connected to an output of the gas sensor. The output of the impedance sensor circuit is a peak voltage that is indicative of the AC voltage drop across the sensor, and ultimately the impedance of the sensing element.

In a further aspect of the invention, this peak voltage is utilized to control the operation of the heating element. In particular, the invention contemplates a closed loop control system in which the thermal output of the heating element is continuously varied to accurately maintain a consistent temperature for the exhaust gas sensor. In one preferred embodiment, a heater controller provides a variable voltage signal to the heating element. The thermal output of the heating element then varies in proportion to the magnitude of the voltage provided by the heater controller. In a further feature of the invention, the heater controller can receive control signals from an engine control module to which the impedance signal of peak voltage value is provided. The engine control module can include software or circuitry that translates the impedance peak voltage value to a voltage to be applied by the heater controller to the heating element. Thus, using this active closed loop control, the thermal output of the heating element may vary widely, while the actual impedance of the exhaust gas sensor should remain fairly constant.

In a specific embodiment of the invention, the impedance sensor circuitry includes a bandpass filter centered around the frequency of the AC signal superimposed on the voltage signal generated by the gas sensor. More particularly, the circuitry includes a high-pass filter, a low-pass filter, and an amplifier. The output from the bandpass filter is provided to a half-wave rectifier, the output of which is the peak voltage signal indicative of the sensor impedance.

It is one object of the invention to provide an exhaust gas sensor that generates an accurate measure of a gas concentration. A more specific object is accomplished by features that allows the gas sensor to generate an accurate measurement value in spite of fluctuations in the exhaust gas temperature.

One benefit of the present invention is that the temperature seen by the exhaust gas sensor can be accurately controlled and maintained using gas sensor impedance feedback in a closed loop control system. Another benefit is that a minimum number of additional components are used.

A more general benefit of the present invention is that interactive control of the accuracy of the exhaust gas sensor means tighter control of the engine air/fuel ratio, which ultimately allows the engine to meet stricter emission requirements and enjoy greater reliability. These and other objects and benefits of the invention will become apparent upon consideration of the following written description and accompanying figures.

DESCRIPTION OF THE PREFERRED EMBODIMENTS

Figure 1:
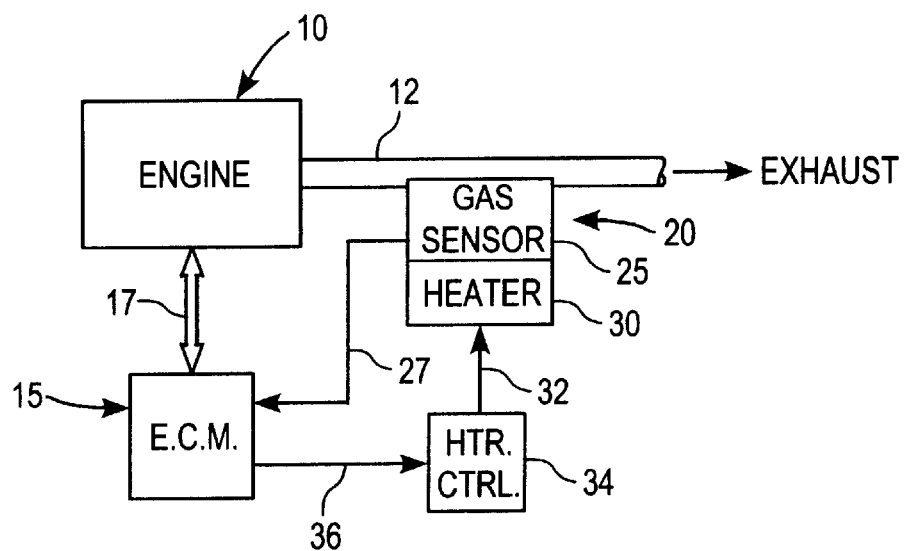
FIG. 1 is a schematic view of an engine with an exhaust gas sensor system.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention contemplates an exhaust gas sensor system for use with an internal combustion engine. For example, as shown in FIG. 1, an engine 10 includes an exhaust conduit 12 through which the gaseous products of combustion are emitted. The engine 10 is controlled by an engine control module 15 that sends and receives signals to and from the engine. In a preferred embodiment, the ECM 15 is a microprocessor-based controller that receives signals from a plurality of engine condition sensors. The ECM 15 then utilizes the signals in a variety of control routines, which routines issue commands or control signals to various operating components of the engine 10.

For example, the ECM 15 controls components that govern the amount of air and fuel that is provided to the cylinders of the engine 10, as well as the timing of ignition of the air/fuel mixture. For most gasoline engines, the routines executed by the ECM 15 attempt to optimize the air/fuel mixture to a stoichiometric ratio to optimize combustion while minimizing noxious emissions. In other applications, such as those using natural gas, the ECM routines are operable to hold the air/fuel mixture to leaner ratios.

As a further feature of the system shown in FIG. 1, an exhaust gas sensor 20 is interposed into the exhaust conduit 12. The gas sensor 20 includes a sensing cell or element 25 that is configured to determine the concentration of particular gaseous components of the exhaust emissions. The sensing element 25 generates an output signal that is provided on line 27 to the ECM 15 that is indicative of a subject gas concentration in the exhaust flow. The sensing element 25 can be a Pt—$ZrO_2$ oxygen sensor that determines the oxygen ($O_2$) concentration within the exhaust flow. Sensors of this type essentially rely upon an electrochemical reaction that modifies the output voltage of the sensor. More specifically, an electrical potential is developed in the sensor from the diffusion of oxygen ions through the sensing element. Various other sensors are contemplated by the present invention, such as a titania-type ($TiO_2$) sensor, as well as sensors configured for determining the concentrations of gases other than oxygen.

In the illustrated embodiment, the exhaust gas sensor 20 also includes a heater or heating element 30. The heating element 30 receives control signals on line 32 from a heater controller 34 that controls the thermal output of the heating element. Specifically, the heating element 30 is disposed immediately adjacent the sensing element 25 to increase the temperature of the element to a preferred predetermined value or temperature range. In this embodiment, the heater controller 34 is itself governed by control signals along line 36 generated by the ECM 15.

Figure 2:
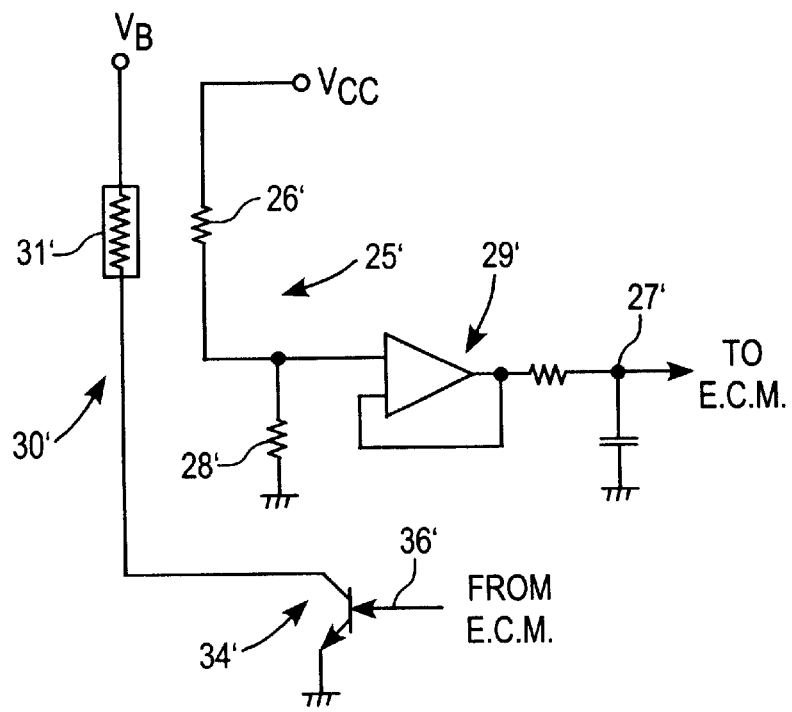
FIG. 2 is a schematic diagram of one form of prior art self-heated exhaust gas sensor device.

Referring now to FIG. 2, a prior art exhaust gas sensor system is depicted. In particular, the sensing element 25' includes an equivalent resistor 26' that corresponds to the electrochemically reactive component of the sensor. A voltage $V_{cc}$ is applied to the sensing element 26' through a resistance network formed by a calibration resistor 28'. The output from this network is fed through a buffer circuit 29' and conveyed to the ECM along output line 27'. In addition, this prior art exhaust gas sensor system includes a resistance component 31' that forms the heating element 30'. In this prior art device, a constant voltage $V_b$, is applied to the heating element 30'. The heater controller 34' constitutes an active circuit component, such as a transistor, that controls current flow through the heating element 30' as a function of control signals from the ECM on line 36'. With this particular system, the heating element 30' is turned off and on as a function of the lean/rich nature of the air-fuel mixture.

Figure 3:
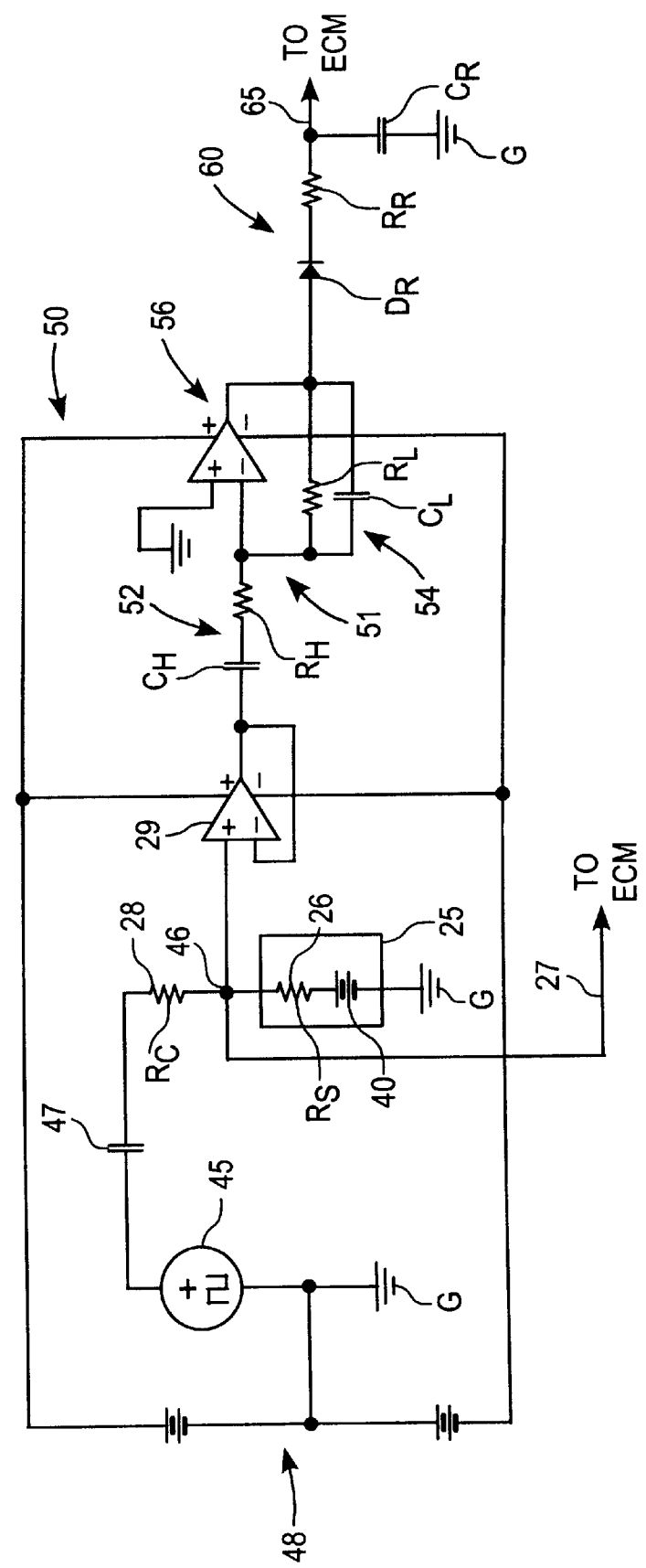
FIG. 3 is a circuit diagram of an exhaust gas sensor system with an impedance sensor according to one embodiment of the present invention.

A system of this type is disclosed in U.S. Pat. No. 5,036,470, issued on Jul. 30, 1991, as illustrated in FIGS. 2 and 3 and described at column 4, line 5–line 66, which description is incorporated herein by reference. As with other prior art systems, the exhaust gas sensor system shown in FIG. 2 relies upon a comparison of the sensor output voltage to various threshold values to determine whether the sensor is at a high or a low temperature. In addition, this prior art system is only capable of gross control levels by turning the heating element 30' off and on in response to this output voltage comparison. One problem faced by the system depicted in the '470 Patent is that its accuracy decays over time as the DC reluctance of the sensor changes due to erosion of the sensor electrodes.

The present invention provides a much more accurate measure of the sensing element performance and a finer degree of control of the heating element than the prior art system shown in FIG. 2. Specifically, with reference to FIG. 3, the sensing element 25 of the exhaust gas sensor 20 includes an equivalent resistance 26 corresponding to the gas sensing or ion diffusion element of the sensor. The sensor can also be idealized by a low frequency or DC output voltage source 40. This idealized voltage source corresponds to the output of the sensing element 25, which in a typical element is the result of an electrochemical reaction. This output voltage is generally low, ranging between 0.0–0.9 volts. For a dual sensor embodiment, the output voltage of idealized source 40 is nominally 0.45V.

The output of the sensing element 25 is provided on line 27 to the ECM 15. More specifically, the output is derived from a node 46 defined between the sensing element 25 and a compensation resistor 28. The compensation resistor 28 essentially forms a voltage divider network with the sensing element 25 to facilitate impedance measurement. The resistor 28 can also be chosen to limit the peak current through the sensing element when it is hot. In the preferred embodiment, the signal on line 27 is an output voltage that is preferably fed to an analog-to-digital converter for use by the ECM 15. This converted value is a direct measure of the gas content in the engine exhaust that is used by control routines to adjust engine performance.

In accordance with the preferred embodiment of the invention, an impedance sensor circuit 50 is provided that is connected to the output node 46 of the sensing element 25. The impedance sensor circuit 50 includes a periodic or AC power supply 45 that is coupled to the voltage divider network through a capacitor 47. The capacitor 47 is included to limit the net bias AC current through the sensing element 25 to essentially 0.0 mA. In the illustrated embodiment, the AC power supply 45 provides a square wave signal at a predetermined frequency and peak-to-peak voltage. In a specific embodiment, the AC signal originates from a TTL+ 5V microprocessor signal to become a 25 kHz±2.5V square wave downstream of the capacitor. The AC power supply 45 can be of a variety known configurations capable of generating a consistent AC signal. For instance, a microprocessor supplied ±2.5V signal can be utilized, in which case the capacitor is no longer necessary. Preferably, the power supply 45 is part of the engine control module 15.

Application of an AC waveform to the sensing element 25 does not disrupt the performance of the sensor itself. The nominal output from the sensing element 25 is essentially a DC voltage, since it is a function of the low frequency fluctuations in exhaust conditions. To the extent that the output at node 46 and on line 27 includes an AC component, a low-pass filter can be integrated between the output line 27 and the input to the ECM 15. This low-pass Filter can have a filter frequency that is significantly lower than the frequency of the signal from the AC power supply 45.

The impedance sensor circuit 50 also includes a DC power supply 48 that is used to power various active circuit components of the sensor 50. For example, the DC power supply 48 powers a buffer amplifier 29 that is connected to the output node 46 of the sensing element 25. The output from the buffer 29 is fed directly to a bandpass filter 51. The bandpass filter 51 is centered about the frequency of the signal generated by the AC signal source 45, and specifically includes a high-pass filter 52 and a low-pass filter 54.

In the specific embodiment for an applied AC signal of 25 kHz, the high-pass filter has a frequency limit of 22.5 kHz, while the low-pass filter has a limit of 28.4 kHz. The bandpass filter 51 thus is focused on the AC signal at node 46 and rejects spurious noise associated with operation of the engine 10 and the low frequency or near DC voltage generated by the sensing element 25. An inverting amplifier 56 is powered by the DC source 48 and applies a gain to the output of the high-pass and low-pass filters. More specifically, the gain from the inverting amplifier 56 is the ratio of the low-pass filter resistor $R_l$ and the high-pass filter resistor $R_h$.

The impedance sensor circuit 50 also includes a half-wave rectifier circuit 60 that receives the output from the bandpass filter 51. The rectifier circuit 60 includes a forward biased diode $D_r$, a resistor $R_r$, and capacitor $C_r$, that are all calibrated so that the output of 65 of the impedance sensor circuit 50 corresponds to the peak value of the AC signal at node 46, or the AC voltage across the sensing element 25.

The output 65 from the impedance sensor circuit 50 constitutes a voltage signal that is indicative of the actual impedance of the sensor element 26. More specifically, the output 65 is a function of the gain at the bandpass filter 51, the half-wave magnitude of the applied AC signal, the value of the compensation resistor 28 and the impedance of the sensor element 26. This value, $V_t$, can be given by the following equation:

$$V_t = \frac{R_h}{R_l} \times \left(\frac{R_s}{R_s + R_c}\right) \times 2.5 - V_d,$$

where $$\frac{R_h}{R_l}$$

is the amplifier gain, $R_s$ is the magnitude of the equivalent resistance 26 in the sensor, and $R_c$ is the value of the compensation resistance 28.

In a specific embodiment of the invention, the high-pass filter includes a resistance $R_h$ of 4.7 kΩ and a capacitance $C_h$ of 0.0015 µF. The low-pass filter can have a resistance $R_l$ of 280 kΩ and a capacitor of 20 pF. With these resistance values, the gain from the bandpass filter 51 is 59.6. In the specific embodiment the reference or compensation resistor 28 has a value $R_c$=12 kΩ. The value $V_d$ is the voltage drop across the rectifier diode $D_r$. This voltage drop $V_d$ is typically temperature dependent and can range from 0.5–0.7V for the normal operating range of the sensor (typically −40 to +120° C.).

As indicated above, the output 65 of the impedance sensor circuit 50 corresponds to a peak value of the applied AC signal as sensed at the node 46. This value then is indicative of the actual impedance $R_s$ of the sensor element 26. In the preferred embodiment, this value is supplied to an A/D converter for input to the ECM 15. Alternatively, the voltage $V_t$ can be further conditioned to remove the voltage drop across the diode, $V_d$, to avoid temperature-based discrepancies.

The ECM can include software that generates a control signal on line 36 to the heater control 34 as a function of the magnitude of the output 65. It is known that the output voltage of the exhaust gas sensor 20 is directly proportional to the temperature of the sensing element. The actual temperature of the sensing element is governed principally by the thermal output of the heating element 30, with temperature variations being proportional to the exhaust gas temperature and flow rate. The output of the heating element 30 is a function of the voltage applied to it by the heater controller 34, as governed by signals received on line 36 from the ECM 15.

Thus, a direct relationship can be established between the magnitude $V_t$, at output signal 65 from the impedance sensor circuit 50 and a control signal on line 36 generated by the ECM 15. More specifically, this relationship provides a measure for modulating the heater voltage to drive the sensor temperature error to zero. The sensor temperature error can be based upon a comparison of the output signal 65 to an optimum impedance value, or upon a comparison of the impedance signal 65 to a prior impedance signal, indicative of a change in exhaust gas sensor impedance. When the impedance of the gas sensor 20 is at its calibrated value, the output signal on line 27 to the ECM 15 accurately reflects the subject gas content. When the impedance strays from this calibrated value, the sensor output signal no longer provides an accurate measure of gas content. The present invention, thus, operates to modulate the temperature of the sensing element 25 to correct the sensor impedance and, therefore, the quality of the output signal 27.

In a preferred embodiment of the invention, the $V_t$ output 65 is initially evaluated at a predetermined temperature, such as 800° C., and a known subject gas content. A baseline value for the equivalent impedance $R_s$ for the sensing element 25 can be determined and correlated to the output 65. For example, a baseline impedance $R_s$ can be 80Ω, which yields a voltage $V_t$ applying the above equation:

$$V_t = 59.6 \times \frac{80}{80 + 12000} \times 2.5 - V_d = 0.987 - V_d = 0.587\,\text{V},$$

for $V_d = 0.4$ V

This value 0.587V for the voltage $V_t$ can represent a baseline value for optimum and accurate performance of the sensing element 25. As the temperature of the sensor 20 increases, the equivalent impedance $R_s$ increases, so the AC voltage drop $V_t$ across the sensor decreases. Likewise, as the sensor temperature decrease, the voltage drop $V_t$. Preferably, the ECM 15 can include software that receives the A/D converted value for the magnitude of $V_t$ and compares that voltage to the baseline voltage for optimum sensor performance. This difference in voltage is indicative of a change in impedance of the sensing element 25, which may be caused by exhaust temperature fluctuations or by degradation of the sensor 20 itself.

In either case, the sensor impedance, and ultimately the output voltage $V_t$, can be corrected or accounted for by changing the temperature of the heating element 30. Most preferably, the ECM software includes means for converting the $V_t$ magnitude signal to a signal on line 36 to the heater controller 34. This signal can be a voltage to be applied to the heating element 30, or a control signal that directs the heater controller appropriately. The output voltage $V_t$ can be converted directly into a voltage on signal line 36, or can be used to determine a differential voltage relative to the baseline value for $V_t$. In either case, the ECM software can implement a table look-up to determine a voltage applied to the heating element 30 based on the magnitude of the output voltage or the differential voltage. The data in the look-up table is preferably calibrated to the baseline conditions of the sensor and is pre-loaded into a memory of the ECM.

Alternatively, the ECM software can implement an equation that translates the voltage magnitude $V_t$ to the signal provided on line 36. The resistor voltage divider network created by the compensation resistor $R_c$ and the sensor impedance $R_s$ leads to a non-linear equation for $V_t$. As a further alternative, the ECM software can be replaced by a circuit that electronically translates the voltage magnitude $V_t$ indicative of sensor impedance $R_s$ to a signal for controlling the output of the heating element 30.

Regardless of the mechanism employed, the goal is to convert the sensor output voltage $V_t$ to modulate the voltage applied on line 36 to the heating element 30 so the sensor impedance stays at its baseline value for optimum performance. Thus, if the voltage $V_t$ decrease the voltage applied to the heating element 30 is proportionately decreased. The decrease in voltage on line 36 decreases the heat output of the heating element 30, which reduces the temperature of the sensing element 25, thereby its impedance to the baseline performance value. Conversely, if the sensor impedance increase, such as due to a drop in exhaust gas temperature, the resulting increase in sensor output voltage $V_t$ can be translated to a stabilizing increase in the thermal output of the heating element 30.

The present invention provides means for adjusting the performance of the exhaust gas sensor 20 to account for changes in exhaust gas conditions (i.e., temperature changes), as well as degradation of the sensing element 25. By establishing the baseline performance condition for the sensing element at a temperature well above the expected exhaust gas temperature, the present invention has plenty of "room" for adjustment of the impedance of the sensing element. This feature is particularly beneficial to correct the negative effects of grain boundary impedance caused by erosion of the electrodes of the sensor.

Use of a superimposed AC signal avoids the impact of DC or low frequency signals associated with the gas content sensor 20. In certain embodiments, the sensor is ambient air referenced so the output voltage of the sensor is indicative of the oxygen (or other gas) partial pressure difference relative to ambient. In these embodiments, no DC bias is required for the sensor. Where the sensor is not ambient air referenced, a DC bias may be necessary for proper performance of the sensing element. In this instance, the AC signal approach of the present invention is not impacted by the DC bias.

The illustrated embodiment depicts a single gas sensor 20. The present invention is equally applicable to dual-cell sensor systems. With these systems, external electronics may be necessary to merge the two sensor outputs to a single output signal $V_t$.

The present invention also provides an active measure of the performance of the sensor 20 in the form of the output voltage $V_t$ on line 65. For instance, the ECM 30 can include a monitoring routine that records and evaluates the magnitude of the voltage signal. The voltage magnitude can be compared to a predetermined value indicative of an unacceptable deterioration in the sensing element 25 and its performance. Since the output voltage $V_t$ represents the sensor impedance, this value can be compared to an impedance value that suggests excessive erosion of the sensor electrodes. Thus, the present invention can alert the technician to replace the gas sensor well before its integrity is compromised. The ECM can include circuitry or software operable to generate a warning or error signal when the voltage magnitude falls outside a predetermined range or exceeds the predetermined value.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed is:

1. A gas sensor system for use in an internal combustion engine, comprising:
   a gas sensor having a sensing element for detecting a gas and operable to generate a gas level signal at an output of said sensor;
   a heating element adjacent said gas sensor operable to generate a continuously variable amount of heat for warming said sensing element in response to variable power applied to said heating element;
   an impedance sensor connected to said output of said sensing element and having circuitry generating an impedance signal as a function of the impedance of said sensor element; and
   control means, connected between said impedance sensor and said heating element, for continuously varying the power applied to said heating element as a function of said impedance signal.

2. The gas sensor system according to claim 1, wherein said control means includes:
   a variable voltage source connected to said heating element, wherein said heating element is responsive to variations in the voltage from said voltage source; and
   means for varying said voltage from said voltage source as a function of said impedance signal.

3. The gas sensor system according to claim 2, wherein said control means includes a memory storing a table of voltage values to be applied to said heating element as a function of said impedance signal.

4. The gas sensor system according to claim 1, wherein:
   said impedance sensor includes a signal source connected to said gas sensor to apply a periodic signal to said sensing element; and
   said circuitry include components operable to determine the magnitude of a periodic output signal sensed at said output of said sensing element, said magnitude corresponding to said impedance signal.

5. The gas sensor system according to claim 4, wherein said circuitry of said impedance sensor includes a bandpass filter centered around the frequency of said periodic signal.

6. The gas sensor system according to claim 5, wherein said circuitry of said impedance sensor includes an amplifier connected to said bandpass filter to apply a gain to the output of said bandpass filter.

7. The gas sensor system according to claim 4, wherein said components of said impedance sensor include a half-wave rectifier.

8. The gas sensor system according to claim 4, wherein said signal source applies a periodic signal having a frequency substantially greater than the frequency of the gas level signal generated by said gas sensor.

9. The gas sensor system according to claim 1, wherein:
said sensing element of said gas sensor has an equivalent impedance; and
said gas sensor includes a voltage divider including said sensing element and a reference resistor, said output of said gas sensor corresponding to a node between said reference resistor and said sensing element.

10. The gas sensor system according to claim 9, wherein said circuitry of said impedance sensor is configured to generate said impedance signal as a function of the ratio of said sensing element impedance and the sum of said sensing element impedance and the value of said reference resistor.

11. The gas sensor system according to claim 1, wherein said control means includes means for comparing said impedance signal to a baseline signal to vary the power applied to said heating element as a function of the result of the comparison.

12. A method for controlling a self-heated gas sensor system, the gas sensor system including a heating element operable to generate a continuously variable amount of heat in response to variable power applied to the heating element, and a sensing element having an equivalent impedance that varies as a function of the temperature of the sensing element, the method comprising:
applying an AC signal to the sensing element;
determining the magnitude of an AC component of the applied signal across the sensing element; and
controlling the power applied to the heating element as a function of the magnitude of the AC component.

13. The method for controlling a self-heated gas sensor system of claim 12, wherein the determining step includes:
sensing the AC signal at an output of the sensing element;
passing the sensed AC signal through a bandpass filter centered about the frequency of the applied AC signal to eliminate spurious noise.

14. The method for controlling a self-heated gas sensor system of claim 12, wherein the determining step includes:
sensing the AC signal at an output of the sensing element;
passing the sensed AC signal through a capacitively coupled half-wave rectifier to generate a magnitude signal.

15. The method for controlling a self-heated gas sensor system of claim 12, in which the sensing element generates a low frequency output signal, wherein said step of applying an AC signal includes applying a signal having a frequency substantially greater than the low frequency output signal.

16. The method for controlling a self-heated gas sensor system of claim 12, wherein said step of controlling the power applied to the heating element includes:
comparing the magnitude of the AC component to a baseline magnitude; and
varying the power applied to the heating element as a function of the result of the comparing step.

17. The method for controlling a self-heated gas sensor system of claim 12, wherein said step of controlling the power applied to the heating element includes:
comparing the magnitude of the AC component to a baseline magnitude; and
determining the power to be applied to the heating element from a look-up table as a function of the result of the comparison step.

18. The method for controlling a self-heated gas sensor system of claim 12, wherein:
said step of controlling the power applied to the heating element includes comparing the magnitude of the AC component to a predetermined limit value indicative of degraded performance of the sensing element; and
the method further comprises the step of generating an error signal when the magnitude exceeds the limit value.

19. A method for detecting exhaust gases from an internal combustion engine, the method comprising:
positioning a gas sensor system, including a heating element operable to generate a continuously variable amount of heat in response to variable power applied to the heating element, and a sensing element having an equivalent impedance that varies as a function of the temperature of the sensing element, in a path of the exhaust gases;
applying an AC signal to the sensing element;
determining a magnitude of an AC component of the applied AC signal across the sensing element; and
applying a variable amount of power to the heating element, wherein the amount of power applied varies as a function of the magnitude of the AC component.

20. The method for detecting exhaust gases from an internal combustion engine of claim 19, wherein the determining step includes:
sensing the AC signal at an output of the sensing element; and
eliminating spurious noise by transmitting the sensed AC signal through a bandpass filter, wherein the bandpass filter is centered about the frequency of the applied AC signal.

21. The method for detecting exhaust gases from an internal combustion engine of claim 19, wherein the determining step includes:
sensing the AC signal at an output of the sensing element;
generating a magnitude signal by passing the sensed AC signal through a capacitively coupled half-wave rectifier.

22. The method for detecting exhaust gases from an internal combustion engine of claim 19, in which the sensing element generates a low frequency output signal, wherein said step of applying an AC signal includes applying a signal having a frequency substantially greater than the low frequency output signal.

23. The method for detecting exhaust gases from an internal combustion engine of claim 19, wherein said step of applying a variable amount of power to the heating element includes:
comparing the magnitude of the AC component to a baseline magnitude; and
varying the amount of power applied to the heating element as a function of the result of the comparing step.

24. The method for detecting exhaust gases from an internal combustion engine of claim 19, wherein said step of applying a variable amount of power to the heating element includes:
comparing the magnitude of the AC component to a baseline magnitude; and
determining the amount of power to be applied to the heating element by utilizing a function of the result of the comparison step as an index to a look-up table.

25. The method for detecting exhaust gases from an internal combustion engine of claim 19, wherein said step of applying a variable amount of power to the heating element includes:

comparing the magnitude of the AC component to a predetermined limit value, the predetermined limit value being indicative of degraded performance of the sensing element; and generating an error signal when the magnitude of the AC component exceeds the predetermined limit value.

* * * * *

UNITED STATES PATENT AND TRADEMARK OFFICE
CERTIFICATE OF CORRECTION

PATENT NO.    : 6,409,969 B1
DATED         : June 25, 2002
INVENTOR(S)   : Streicher et al.

It is certified that error appears in the above-identified patent and that said Letters Patent is hereby corrected as shown below:

<u>Column 9,</u>
Line 25, delete "a" and insert -- said --.
Line 25, delete "signal" and insert -- impedance value --.

Signed and Sealed this

Eleventh Day of February, 2003

JAMES E. ROGAN
*Director of the United States Patent and Trademark Office*